United States Patent
Zhang et al.

(10) Patent No.: US 7,619,103 B2
(45) Date of Patent: Nov. 17, 2009

(54) ARYLATION AND THE SKELETAL ISOMERIZATION OF FATTY ACID AND ALKYL ESTERS THEREOF USING METAL ION EXCHANGED SOLID MATERIALS AS CATALYST

(75) Inventors: Zongchao Zhang, Richland, WA (US); Shuguang Zhang, New Rochelle, NY (US); James F. Gadberry, Danbury, CT (US)

(73) Assignee: Akzo Nobel N.V., Arnhem (NL)

( * ) Notice: Subject to any disclaimer, the term of this patent is extended or adjusted under 35 U.S.C. 154(b) by 178 days.

(21) Appl. No.: 10/565,549

(22) PCT Filed: Jul. 16, 2004

(86) PCT No.: PCT/EP2004/008008

§ 371 (c)(1),
(2), (4) Date: Jan. 23, 2006

(87) PCT Pub. No.: WO2005/014766

PCT Pub. Date: Feb. 17, 2005

(65) Prior Publication Data

US 2007/0015928 A1    Jan. 18, 2007

Related U.S. Application Data

(60) Provisional application No. 60/489,423, filed on Jul. 24, 2003.

(51) Int. Cl.
*C11C 3/14* (2006.01)
(52) U.S. Cl. .................................................. 554/125
(58) Field of Classification Search ................ 554/125
See application file for complete search history.

(56) References Cited

U.S. PATENT DOCUMENTS

| | | | |
|---|---|---|---|
| 2,275,312 A | 3/1942 | Tinker et al. ............. 260/515 |
| 3,192,239 A | 6/1965 | Ault et al. ............... 260/399 |
| 3,251,897 A | 5/1966 | Wise .................... 260/671 |
| 3,865,894 A | 2/1975 | Kirsch et al. .......... 260/683.43 |
| 5,034,161 A * | 7/1991 | Alink .................... 554/162 |
| 5,440,059 A * | 8/1995 | Alink .................... 554/220 |
| 5,686,935 A | 11/1997 | Weisbrod ............... 345/100 |
| 5,817,831 A | 10/1998 | Rhubright et al. ......... 548/447 |
| 5,840,942 A * | 11/1998 | Oude Alink ............. 554/162 |
| 2003/0100780 A1* | 5/2003 | Zhang et al. ............ 554/125 |

FOREIGN PATENT DOCUMENTS

GB    1120309       7/1968
WO    WO 03/006157 A2    1/2003

OTHER PUBLICATIONS

International Search Report, No. PCT/EP2004/008008, Oct. 26, 2004.
Kohashi et al., "Addition of Aromatic compounds to Oleic Acid Catalyzed by Heterogeneous Acid Catalysts," JAOCS, vol. 61, No. 6, pp. 1048-1051 (Jun. 1984).
Zhang et al., "Strongly Acid and High-Temperature Hydrothermally Stable Mesoporous Aluminosilicates with Ordered Hexagonal," Angew. Chem. Int. Ed. 40, No. 7, pp. 1258-1262 (2001).
Zhange et al., "Mesoporous Aluminosilicates with Ordered Hexagonal Structure, Strong Acidity, and Extraordinary Hydrothermal Stability at High Temperatures," J. Am. Chem. Soc., 123, pp. 5014-5021 (2001).
Han et al., "A Novel method for Incorporation of Heteroatoms into the Framework of Ordered Mesoporous Silica Materials Synthesized in Strong Acidic Media," J. Phys. Chem. B, 105, pp. 7963-7966 (2001).
Liu et al., "Steam-Stable Aluminosilicate Mesostructures Assembled from Zeolite Type Y Seeds," J. Am. Chem. Soc., 122, pp. 8791-8792 (2000).
Liu et al., "Steam-Stable MSU-S Aluminosilicate Mesostructures Assembled from Zeolite ZSM-5 and Zeolite beta Seeds," Angew. Chem. Int. Ed., 40, No. 7, pp. 1255-1258 (2001).
Han et al., "Hydrothermally Stable Ordered Hexagonal Mesoporous Aluminosilicates Assembled from a Triblock Copolymer and Preformed Aluminosilicate Precursors in Strongly Acidic Media," Chem. Mater., 14, pp. 1144-1148 (2002).
Smith et al., "Isomeric Arylstearic Acids," Eastern Regional Research Laboratory, vol. 30, pp. 885-888 (Mar. 1965).
Smith et al., "Phenylstearic Acids and Related Compounds Isolation of 17-, 16-, 15- and 13-Phenyl Isomers[1]," Journal of the American Oil Chemist's Society, vol. 48, pp. 160-162 (Apr. 1971).
Smith et al., "Isomeric Phenylstearic Acids and Related Compounds: Composition and Partial Separation[1]," Journal of the American Oil Chemist's Society, vol. 45, pp. 747-749 (Nov. 1968).
Nakano et al., "Methanesulfonic Acid Catalyzed Addition of Aromatic Compounds to Oleic Acid," Journal of American Oil Chemist's Society, vol. 61, No. 3, pp. 569-573 (Mar. 1984).

* cited by examiner

*Primary Examiner*—Deborah D Carr
(74) *Attorney, Agent, or Firm*—Ralph J. Mancini

(57) ABSTRACT

The present invention generally relates to a process for the arylation of unsaturated linear fatty acids and/or alkyl esters thereof to their aryl branched counterparts. Said arylation process comprises contacting said unsaturated linear fatty acids and/or alkyl esters thereof and one or more aromatic compounds with at least one metal ion exchanged solid material catalyst. The invention also relates to various derivatives prepared from the aryl branched fatty acids and/or alkyl esters prepared in accordance with the present invention.

12 Claims, No Drawings

ARYLATION AND THE SKELETAL ISOMERIZATION OF FATTY ACID AND ALKYL ESTERS THEREOF USING METAL ION EXCHANGED SOLID MATERIALS AS CATALYST

This case was filed under the Patent Cooperation Treaty on Jan. 23, 2006 and claims priority of U.S. provisional application Ser. No. 60/489,423 filed on Jul. 24, 2003.

FIELD OF THE INVENTION

The present invention generally relates to solid acidic materials as catalysts and to the use of said catalysts for the arylation and the isomerization of fatty acids and/or alkyl esters thereof. The invention also relates to the aryl branched acids and aryl alkyl esters prepared by the aforementioned process.

BACKGROUND OF THE INVENTION

Fatty acids and alkyl esters thereof are the building blocks for various compositions ranging from lubricants, polymers, solvents, cosmetics and the like. Fatty acids are generally obtained by hydrolysis of triglycerides of vegetable or animal origin. Naturally occurring triglycerides are esters of glycerol and generally straight chain, even numbered carboxylic acids, in size ranging from 10-24 carbon atoms. Most common are fatty acids having 12, 14, 16 or 18 carbon atoms. The fatty acids are either saturated or contain one or more unsaturated bonds.

Long, straight chain saturated fatty acids (C10:0 and higher) are solid at room temperature, which makes them difficult to process in a number of applications. Unsaturated long chain fatty acids, however, e.g. oleic acid are liquid at room temperature, so are easy to process, but are unstable because of the existence of double bond(s). Branched fatty acids mimic the properties of the straight chain unsaturated fatty acids in many respects, but do not have the disadvantage of being unstable. "Branched fatty acids" means fatty acids containing one or more alkyl side groups, and/or aryl groups, which are attached to the carbon chain backbone at any position. Therefore, branched fatty acids are for many applications more desirable than straight chain fatty acids. Commercial branched acids are not, however, naturally occurring materials.

In one process U.S. Pat. Nos. 5,440,059 and 5,840,942 describe the reaction of xylene and oleic acid using acidic clay as catalyst. Clay to oleic ratio (wt/wt) is from 2 to 0.6; xylene to oleic ratio (wt/wt) is up to 20. The reaction temperature range is from 130-250° C., but large amount of dimer and heavy acids were formed at high temperature.

Kohashi's paper (JAOCS, Vol. 61, no. 6, June 1984) showed that acidic clay also catalyzes the addition of phenol to oleic acid, but the reaction of toluene with oleic acid was very slow to catalyze.

U.S. Pat. No. 5,840,942 discloses a method for preparing an aryl-substituted fatty acid or fatty ester. The method involves the use of zeolite or certain clay catalysts. The clay catalysts are acid clay catalysts of the type known for their usefulness in dimmer acid synthesis.

Finally, U.S. Pat. No. 5,034,161 discloses reactions between toluene, xylene, phenol and oleic acid catalyzed by Nafion catalyst NR-50, available from E.I. du Pont. The Nafion catalyst is believed to be a perfluorinated resin treated with sulfonic acid.

However, all of these processes are plagued by low yield and/or a high rate of undesirable byproduct formation. Accordingly, there is a need for an improved process that overcomes these disadvantages, i.e. a process for the preparation of aryl branched fatty acids from straight chain unsaturated fatty acid feedstocks comprising at least one aryl compound with a high conversion rate, an increased selectivity towards branched monomeric isomers and which employs a reusable catalyst.

SUMMARY OF THE INVENTION

The present invention relates to a process for the alkylation of one or more aromatic compounds with unsaturated fatty acids to aryl side branched fatty acids. This process comprises contacting unsaturated linear fatty acids and/or esters thereof and aromatic molecules with at least one solid acidic catalyst. The invention also relates to various derivatives prepared from the aryl branched fatty acids and/or esters prepared in accordance with the present invention.

DETAILED DESCRIPTION OF THE PRESENT INVENTION

The present invention relates to the use of solid acid catalysts for the addition of aryl compounds to unsaturated fatty acids (arylation) and the isomerization of unsaturated fatty acids. The acid catalysts are highly active and reusable after simple treatment. The arylation and isomerization (alkylation) may occur concurrently; arylation may also follow isomerization to branched unsaturated fatty acids. The balance between arylation and isomerization can be adjusted by tuning the catalyst acidity and/or reaction conditions. Under conditions employed in this invention, little cracking was observed and a small amount of lactone and ketone was formed.

The process comprises contacting unsaturated linear fatty acids and/or methyl esters thereof, and one or more aromatic compounds, with at least one solid acidic catalyst. The catalyst and process of the invention advantageously converts fatty acid and/or alkyl ester feedstock into a mixture that is rich in aryl branched fatty acids and/or aryl branched alkyl esters and low in oligomers. While the reaction products of the present process will generally comprise both saturated as well as unsaturated products, and both are thus included in the invention, there is high selectivity towards the formation of aryl branched fatty acids and/or aryl branched alkyl esters.

The invention also relates to various derivatives prepared from the aryl branched fatty acids and/or alkyl esters prepared in accordance with the present invention.

The solid acidic catalyst and/or support material of the invention is characterized in that it provides the acidic sites for the isomerization of unsaturated fatty acids. Optionally, metals can be loaded on such acidic support materials to allow for subsequent hydrogenation of the aryl branched unsaturated fatty acids to saturated ones.

Acidic zeolites are a preferred acid support material. Zeolites are crystalline aluminosilicates generally represented by the formula

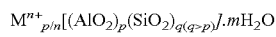

where M is a metal cation of groups IA including Hydrogen or IIA and n is the valency of this metal. Zeolites consist of a network of $SiO_4$ and $AlO_4$ tetrahedra linked together via shared oxygen atoms. Aluminum has a $3^+$ valency resulting in an excess negative charge on the $AlO_4$ tetrahedra, which can be compensated by cations such as $H^+$. When M is hydrogen the materials are Bronsted acidic, when M is for example Cs the materials are basic. Upon heating, Bronsted acidic hydroxyls condense creating coordinately unsaturated Al, which acts as a Lewis acid site. The acid strength, acid site density and Bronsted versus Lewis acidity are determined by the level of framework aluminum. The ratio of silica/alumina can be varied for a given class of zeolites either by controlled calcination, with or without the presence of steam, optionally followed by extraction of the resulting extra framework aluminum or by chemical treatment employing for example ammonium hexafluorosilicate.

As zeolite frameworks are typically negatively charged, the charge balancing cations related to this invention include monovalent cations such as $H^+$, $Li^+$ and the like, divalent cations such as $Mg^{2+}$, $Zn^{2+}$ and the like and trivalent cations such as $Ln^{3+}$, $Y^{3+}$, $Fe^{3+}$, $Cr^{3+}$ and the like. The framework composition of the three-dimensional zeolites may contain other elements in addition to Al and Si, such as, for example, P, Ti, Zr, Mn, and the like. Although any zeolite meeting the parameters of this embodiment of the present invention can be employed, faujasite (e.g. Y zeolite), Beta zeolite, Offeretite and the like are particularly well suited for the present process. The Si/Al ratio of the zeolites can vary depending on the particular zeolite employed provided that the skilled artisan understands that a ratio which is too low will result in more by-products and a ratio which is too high will lower the activity of the zeolite. In most cases the Si/Al ratio of the zeolites is at least 2, up to at least 20 and higher. For example, the Si/Al ratio for Beta zeolite may be from about 5-75 while that for Y zeolite can be from 2 to about 80.

Zeolites usefully employed within the embodiments of the invention are typically acidic zeolites with or without metal ions, in addition to protons. Specific examples of zeolite structures include, but are not limited to faujasite, mordenite, USY, MFI, Mor, Y and Beta types.

It is to be understood that if said acidic zeolites are not loaded with metal ions, then a separate catalyst loaded with at least one metal capable of hydrogenating the branched unsaturated fatty acids may optionally be employed.

Additionally, the acid zeolite catalyst employed in the process of the present invention must have a pore size sufficiently large so as to accommodate both the fatty acid and the aromatic. Because the arylation/isomerization takes place within the pores of the zeolite catalyst, zeolites with small apertures are not suitable as they cannot allow the entry of the fatty acid and/or the aromatic. This is in stark contrast to acidic clay catalysts where the arylation is conducted on the surface of such catalysts since they do not contain pores.

In one embodiment, the zeolites employable in the context of the present invention include all those with 10-ring structures and higher-ring zeolite structure types with 1-dim and 3-dim. Examples include, but are not limited to, AEL, AFO, (and others in 10-ring, 1-dim, none), FER, (and other 10-ring, 1-dim, 1-dim), MFI, MEL, MEN, and all the higher ring zeolite types.

In another embodiment, the acidic zeolite of the invention is characterized in that it comprises a material having a three dimensional pore structure wherein

| Biggest ring | Channel dimension | none | 7-ring | 8-ring (Second biggest ring) | | 10-ring | | 12-ring |
|---|---|---|---|---|---|---|---|---|
| | | — | 1-dim | 1-dim | 3-dim | 1-dim | 2-dim | 1-dim |
| 6-ring | — | AFG, AST, DOH, LIO, LOS, LTN, MEP, MTN, NON, SGT, SOD | | | | | | |
| 8-ring | 1-dim | ABW, AFT, ATN, ATV, AWW, BIK, CAS, DDR, EAB, ERI, JBW, LEV | | AEI(i), APC(i), APD(i), ATT(i), BRE(i), EDI(i), GIS(i), GOO(i), MER(i), MON(i), PHI(i), THO(i), YUG(i) | | | | |
| | 3-dim | ANA, CHA, LTA | | NAT(i) | KFI(c), PAU(c), RHO(c) | | | |
| 9-ring | 1-dim | CHI | | LOV(i) | | | | |
| 10-ring | 1-dim | AEL, AFO, EUO, LAU, MTT, NES, PAR, TON | | DAC(i), EPI(i), FER(i), HEU(i), MFS(i), STI(i) | | | MFI(i) | |
| | 3-dim | MEL | | WEN(i) | | | | |
| 12-ring | 1-dim | AFI, ATO, ATS, CAN, LTL, MTW, ROG | MEI(i) | AFR(i), AFS(i), AFY(i), BPH(i), GME(i), MAZ(c), MOR(i), OFF(i) | | BOG(i) | | EMT(i) |
| | 3-dim | FAU | | | | | | BEA(i) |
| 14-ring | 1-dim | AET, UTD-1* | | | | | | BEA(i) |
| 18-ring | 1-dim | VFI | | | | | | |
| 20-ring | 3-dim | | | | CLO(c) | JDF-20(i)* | | |

(i) = channels intersect
(c) = channels cross without intersecting
* = structure code not yet defined at least one of the channel structures has a pore size large enough to allow diffusion of the branched fatty acids and/or alkyl esters thereof. More particularly, at least one of the channel structures has a pore size large enough for the fatty acid and/or alkyl ester to enter the pore and access the internal active sites. Typically, this pore size is at least about 5.5 Å, preferably at least 6.0 Å. Catalysts of this type having a three-dimensional channel structure have higher activity and are not as readily deactivated by pore mouth blockages compared to catalysts having one and/or two dimensional channel structures. Zeolites employable in the present process comprise a three-dimensional pore structure wherein at least one channel structure has a pore size large enough to allow diffusion of the branched fatty acids and/or alkyl esters thereof. In general, the larger the number of oxygen atoms in the ring opening, the larger the pore size of the zeolite. But this size is also determined by the structural shape of the ring. Zeolite materials having a three-dimensional channel structure and a pore size of at least about 6.0 Å can generally be employed in the process of the invention. Such pore structures having a pore size of at least about 6.0 Å generally comprise 10 and/or 12 membered rings, or even larger rings in their structures.

It is known that zeolites having a three dimensional channel structure can be formed by zeolites having one dimensional channel with certain mineral acids such as nitric acid, hydrochloric acid and the like, and/or certain organocarboxylic acids such as acetic acid and oxylic acid and the like. Other methods for generating zeolites with a three dimensional channel structure are known to the skilled artisan.

In still another embodiment, the invention contemplates a process the invention utilizes mesoporous aluminosilicates. However, other mesoporous materials based on other materials such as those comprising transition metals and post transition metals can also be employed. Catalytic materials such as those employable in the context of the present invention are described in Angewandte Chemie Int. Ed. (7, 2001, 1258), J. Am. Chem. Soc. (123, 2001, 5014), J. Phys. Chem. (105, 2001, 7963), J. Am. Chem. Soc. (122, 2000, 8791), Angew. Chem. Int. Ed. (40, 2001, 1255), and Chem. Mater. (14, 2002, 1144) and in Chinese Patent Application No. 01135624.3, which are incorporated herein by reference.

Generally, the synthesis of the mesoporous aluminosilicates and aluminophosphates of the present invention involves the preparation of primary and secondary zeolite building unit precursors, which are subsequently assembled to stable mesoporous zeolites in the presence of surfactant or polymeric templates. Mesoporous zeolites derived from this invention have similar acidity, thermal and hydrothermal stability as conventional zeolites, and also have high catalytic activity.

As an example, highly ordered hexagonal mesoporous aluminosilicates (MAS-5) with uniform pore sizes were synthesized from an assembly of preformed aluminosilicate precursors with cetyltrimethylammonium bromide (CTAB) surfactant. Choice of surfactant is not a limiting feature as most quaternary ammonium salts, phosphonium salts, anionic and non-ionic surfactants, and polymers which form micellar structures in solution are effective. Other examples include, but are not limited to cetyltrimethylphosphonium, octyldecyltrimethylphosphonium, cetylpyridinium, myristyltrimethylammonium, decyltrimethylammonium, dodecyltrimethylammonium, dimethyldidodecylammonium, fatty alkylamines, fatty acids, and mixtures thereof.

The aluminosilicate precursors were obtained by heating aluminosilica gels from the aqueous hydrolysis of aluminum and silicon precursors. As previously mentioned, the present invention is not limited to Al and Si precursors, and other precursors such as certain transition metal candidates can be employed. The aluminosilicate gels are heated at 80°-400° C. for 2-10 hours. The gels had a $Al_2O_3/SiO_2/TEAOH/H_2O$ molar ratio of 1.0/7.0-350/10.0-33.0/500-2000. Mesoporous MAS-5 shows extraordinary stability in both boiling water and steam. Additionally, temperature-programmed desorption of ammonia shows that the acidic strength of MAS-5 is much higher than that of conventional mesoporous materials and is comparable to that of microporous Beta zeolite. Analysis and testing of the materials of the present invention suggest that MAS-5 consists of both mesopores and micropores and that the pore walls of the MAS-5 contain primary and secondary structural building units similar to those of microporous zeolites. The unique structural features of the mesoporous aluminosilicates of the present invention are believed to be responsible for the observed strong acidity and high thermal stability of the mesoporous mesoporous aluminosilicates of well ordered hexagonal symmetry.

Within this embodiment of the invention, the invention is not limited to zeolites in general, or to a particular zeolite, as materials other than zeolites can be employed in conjunction with the mesoporous materials of the invention. Zeolites are, however, a preferred material to be employed with the mesoporous materials of this embodiment and the use of any known or yet to be discovered zeolites in the formation of the mesoporous materials of the present invention is included within the scope of the present invention. More particularly, using precursors of other zeolite structures, one of ordinary skill in the art could readily tailor make mesoporous zeolites containing the structural features of the particular zeolite chosen. Examples of zeolites which can be employed in the context of the present invention include, but are not limited to, zeolite A, Beta zeolite, zeolite X, zeolite Y, zeolite L, zeolite ZK-5, zeolite ZK-4, zeolite ZSM-5, zeolite ZSM-11, zeolite ZSM-12, zeolite ZSM-20, ZSM-35, zeolite ZSM-23, aluminophosphates including but not limited to VPI-5 and the like, and mixtures thereof, and/or zeolitic materials having the following framework structures: AEL, AFO, AHT, BOG, CGF, CGS, CON, DFO, FAU, FER, HEU, AFS, AFY, BEA, BPH, CLO, EMT, FAU, GME, MOR, MFI, and the like.

It is known that the aluminosilicates and/or aluminophosphates can be metal containing, or non-metal containing. Within the context of this embodiment of the invention, zeolites may contain elements such transition metals, post transition metals, Ln series and the like. Specific examples include, but are not limited to B, Ti, Ga, Zr, Ge, Va, Cr, Sb, Nb, and Y.

In still another embodiment, the catalyst of the invention is a metal ion exchanged material comprising zeolites, clays, resins, amorphous oxides, molecular sieves or their mixtures. The metal ions can be from a single metal or from multiple metals, with or without other additives. The sources of metal ions can be from any salts containing the metal ions with or without ligands. Mixed metal ions or their complexes with various ligands can be used. Ion exchange can be carried out in an aqueous phase, or in the absence of aqueous phase, e.g. solid state exchange by physically mixing the solid materials with one or more metal ion containing salts followed by calcination at elevated temperature. The ion exchange level can range from trace metal ions to 100% metal ion level based on ion exchange capacity. Ion exchange to a level over 100% of ion exchange capacity can also result in active catalysts.

As an example, acidic proton form ($H^+$) zeolites, such as HZSM-5, H-Mordenite, HBeta, and HY, are known to be active for the isomerization of unsaturated fatty acids to branched fatty acids. Proton form zeolites containing group VIII zero valent metals are also active catalysts as zero valent metals do not affect the overall proton concentrations in zeolites. When positively charged protons are replaced by metal ions, the overall proton concentrations decrease. As isomerization is known to typically take place via protonated carbenium ion mechanism, the concentration and strength of proton acidity are critical for skeletal isomerization activity of proton form zeolites.

In the context of the present invention the inventors have discovered that metal ion exchanged zeolites are highly active for the skeletal isomerization of unsaturated fatty acids, even at near or over 100% ion exchange. This is particularly unexpected based on conventional wisdom as the concentration of protons is significantly reduced if not completely eliminated. It is preferred that higher valent metals be employed in the catalysts of the claimed invention. By higher valent metals it is meant that the valency of the metal(s) must be greater than zero. Most divalent and trivalent metal ions from the periodic table showed improved catalytic activity over purely proton form zeolites toward the isomerization and aryl branching of unsaturated fatty acids. The activity varies with the type of cation and the degree of ion exchange.

The higher valent metals that can be exchanged on the catalyst of this embodiment of the claimed invention are non-rare earth metals including, but not limited to: $Li^+$, $Cu^+$, $Rh^+$, $Ir^+$, $Mg^{2+}$, $Ca^{2+}$, $Mn^{2+}$, $Fe^{2+}$, $Co^{2+}$, $Ni^{2+}$, $Cu^{2+}$, $Zn^{2+}$, $Sr^{2+}$, $Mo^{2+}$, $Pd^{2+}$, $Sn^{2+}$, $Pt^{2+}$, $Sc^{3+}$, $Cr^{3+}$, $Fe^{3+}$, $Co^{3+}$, $Ga^{3+}$, $Y^{3+}$, $Nb^{3+}$, $Ru^{3+}$, $Rh^{3+}$, $Ir^{3+}$, $Bi^{3+}$, $Ti^{4+}$, $Mn^{4+}$, $Zr^{4+}$, $Mo^{4+}$, $Sn^{4+}$, $V^{5+}$, $Nb^{5+}$, $Mo^{6+}$, mixtures thereof and the like.

In yet another embodiment the catalyst of the invention is a phosphated, sulfated, and/or tungstated zirconia optionally doped with at least one transition metal, rare earth metal, and the like.

In still yet another embodiment the catalyst of the invention is a heteropolyanions based solid acid, also known as acidic polyoxometallates. Heteropolyacids are acidic polyoxometallates with at least one another element in addition to W, Mo, V, Nb, Ta, or U in the anions. Typical examples of heteropolyacids include, but not limited to the following:

$H_4PMo_{11}VO_{40}$ $K_xH_{4-x}PMo_{11}VO_{40}$ $H_5PMo_{10}V_2O_{40}$ $(NH_4)_6P_2Mo_{18}O_{62}$ $H_3PMo_{12}O_{40}$, $H_3PW_{12}O_{40}$ $H_4SiW_{12}O_{40}$, $H_4SiMo_{12}O_{40}$ $H_9P_2V_3W_{15}O_{62}$ $H_5PMo_{10}V_2O_{40}$ $H_6P_2W_{18}O_{62}$ $H_3PMo_6W_6O_{40}$ $H_5PV_2Mo_{10}O_{40}$

Finally, metal triflate type of lewis acid catalysts can also be usefully employed as a catalyst in the process of the present invention.

Good selectivity and conversion can be obtained by the process of the present invention if at least part of the isomerization or arylation is performed at a temperature of between about 100° C. and 350° C. In another embodiment, the process of the invention is performed at a temperature of between about 230° C. and 285° C. Since the conversion is also a function of the reaction/contact time, it is preferred that the fatty acid feedstock is contacted with the catalyst for a period of at least 5 minutes and reaction times of 1-16 hours are typical. An even longer period could be used if the process is operated at a lower temperature.

In general, the amount of catalyst employed in the process according to the invention is between 0.01 and 30% by weight when the process is carried out in batch or semi-batch process, based on the total reaction mixture. In another embodiment the amount of catalyst used between 0.5 and 10% by weight. In still another embodiment the catalyst amounts are between 1 and 5% by weight.

The processes of the present invention can be performed both in batch and fixed bed continuous processes. Good selectivity and conversion can be obtained by the process of the present invention if at least part of the isomerization is performed at a temperature of between about 100° C. and 350° C. In another embodiment, the process of the invention is performed at a temperature of between about 230° C. and 285° C. Since the conversion is also a function of the reaction/contact time, it is preferred that the feedstock is contacted with the catalyst for a period of at least 5 minutes and reaction times of 1-16 hours are typical. An even longer period could be used if the process is operated at a lower temperature.

When a continuous flow reactor is employed, the weight hour space velocity is between 0.01 and 100. Weight hour space velocity is defined as the weight of feed in grams passing over one gram of catalyst per hour.

Additionally, it has been found that by using a catalyst system according to this invention it is possible to reuse the catalyst. In some cases it may be desired to add fresh catalyst while optionally removing a part of the spent catalyst, and in other cases regeneration of the catalyst may be desired. Regeneration can be effected by various methods know to the skilled artisan. For example, regeneration can be accomplished by utilizing controlled oxidative regeneration and/or by washing with a solvent.

Typical feedstocks comprise fatty acids and esters derived from natural fats and oils. Such feedstocks are predominantly unsaturated linear alkylcarboxylic acids, related esters or mixtures thereof, optionally containing other organics. Since the present process is designed for isomerization or conversion of unsaturated fatty acids and/or alkyl esters into their branched counterparts, it is beneficial if the comprises of at least about 30% by weight of said unsaturated fatty acids and/or alkyl esters. In another embodiment, the feedstock comprises at least 50% by weight of unsaturated fatty acids and/or alkyl esters. Any unsaturated and/or polyunsaturated fatty acid and/or alkyl esters, or mixtures thereof is suitable as a feedstock in accordance with the present invention. In one embodiment, the feedstock comprises oleic acid as the unsaturated fatty acid and/or the alkyl ester of oleic acid in an amount of at least 40% by weight, preferably at least 70% by weight.

The feedstock also comprises at least one aryl compound. Generally, the aryl compound is an aromatic that contains at least six (6) carbon atoms in the aromatic ring. Aromatic compounds are benzene and those compounds that resemble benzene in chemical behavior. For example, such compounds tend to undergo ionic substitution rather than addition and they share a similarity in electronic configuration. The aryl compound can be substituted or unsubstituted and the aromatic ring may also contain one or more heteroatoms. Preferred aryl compounds include, but are not limited to benzene, toluene, xylene, cumene, aniline, phenol, cymene, styrene, mesitylene, mixtures thereof and the like.

The products of the present invention comprise both arylated and branched fatty acids. The typical ratio of aryl:branched of the products of the present invention is from about 1:1 to about 1:2.

Additionally, the invention contemplates all derivatives prepared from branched fatty acids and alkyl esters prepared by the processes described herein.

Fatty acid alkyl esters and fatty acids are versatile building blocks and conversion of these materials into a wide variety of other surfactants is possible. Some examples of the type of reactions possible are listed below. From these starting materials it is possible to produce non-ionic, anionic and cationic surfactants, all of which is within the scope of the present invention.

The aryl branched fatty acid alkyl esters and fatty acids products of the present invention can be utilized as starting materials to prepare the same derivatives as their linear counterparts. For example, the aryl branched alkyl esters of the present invention are readily converted into fatty acid glucamides and glycerol esters. Alkylation of polyhydridic molecules is possible. An example of this type of reaction would be reaction of a branched methyl ester with sucrose to prepare sucrose esters. Conversion of branched alkyl esters to alpha sulfonates is known. For example, branched fatty acid ester sulfonates (FAES) can be produced from branched methyl esters by sulfonation, followed by bleaching and neutralization. Branched fatty acid alkyl esters can also be converted into other branched alkyl esters by a transesterification reaction. In most cases, the smaller molecular weight alcohol is removed from the reaction mixture forcing the reaction to the desired products.

Branched fatty acids undergo many of the same reactions their linear counterparts as well as linear and branched fatty acid alkyl esters. For example, the branched fatty acid of the present invention may be converted into its' soap form by neutralization with a base. N-acyl sarcosinates can be prepared from reaction of the branched fatty acid of the present invention fatty acid or its derivatives with sarcosine. Acylated protein hydrolysates are prepared by acylation of protein hydrolysates with branched fatty acids or acid chlorides. The hydrolysates are variable in composition, depending on how they are prepared. These are mild surfactants used in often in personal care formulations. 2-Sulfoethyl esters of branched fatty acids, also known as acyl isethionates, are excellent surfactants. This family tends to be mild to the skin and hard water tolerant. Amido propyl amine and derivatives are prepared from the fatty acid or fatty acid alkyl ester. This family of surfactants has seen commercial application in laundry detergents, dishwashing liquids and many personal care formulations. Condensation of a fatty acid alkyl ester or fatty acid with an alkanolamine results in the formation of an alkanolamide. The alkanolamide and it derivatives have a variety of uses commercially depending on its specific chemical structure. Ethoxylated alkanolamides are used as compatibilizers in formulations. Many alkanolamides and derivatives are used as thickeners and foamers. Branched fatty acids can be alkoxylated with ethylene oxide, propylene oxide and butylenes oxide to make a useful family of non-ionic surfactants. Branched fatty acids can be converted into nitriles which are the building blocks for a large variety of cationic and amine surfactants. Branched fatty acids acan also be used in a reaction to prepare esteramines which are quaternized, esterquats. The major use of esterquats is in household fabric softeners.

Conversion of the branched alkyl esters and branched fatty acids into branched alcohols can also be done. The alcohol is another building block to prepare other types of surfactants. Alcohols are used to prepare alkyl polyglycosides (APGs). These materials offer a hydrophile based on a natural sugar. Conversion of the alcohol into amines and quaternaries occurs readily and is a commercially important reaction in the preparation of cationic surfactants. Non-ionic surfactants are prepared by alkoxylation of alcohols. Common alkoxylation agents are ethylene oxide, propylene oxide and butylene oxide. Conversion of alcohols (with or without alkoxylation) to alcohol sulfates is a commercially important process. The use of alcohol sulfates in laundry is increasing especially in Europe. Other areas of use include shampoos, textile processing and emulsion polymerization. Alcohols can also be converted in phosphate esters. Both mono and diphosphate esters can be favored depending on the reaction conditions. Polyalkoxycarbonates are produced by the reaction of sodium chloroacetate with an alcohol ethoxylate, or from acrylic acid and an alcohol ethoxylate. These can also be made by direct oxidation of the alcohol ethoxylate under carefully controlled conditions.

The aforementioned description is merely illustrative and not intended to limit the scope of the invention. Accordingly, one of ordinary skill in the art would readily recognize that the branched products of the present invention, like their linear counterparts, can be readily employed as starting materials in the preparation of numerous derivatives as illustrated by the following chart. Any and all of the derivatives prepared from the novel products of the present invention are within the scope of the present invention.

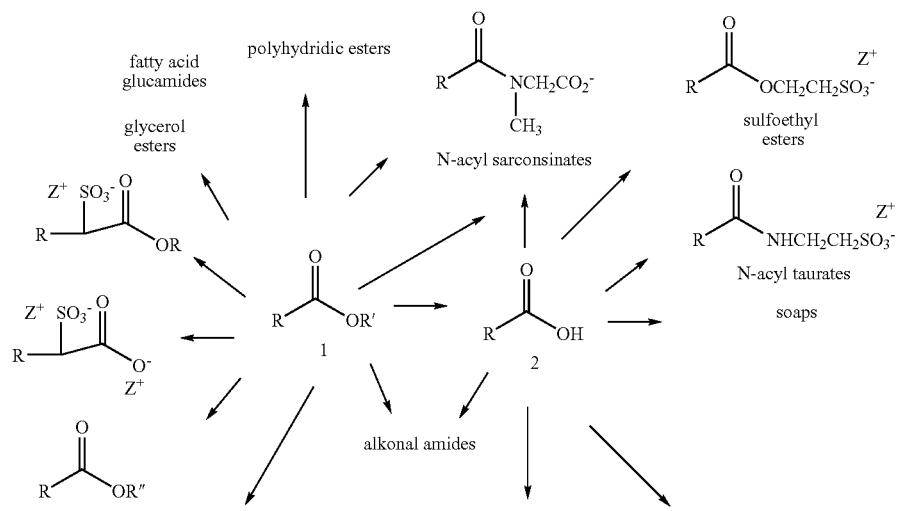

-continued

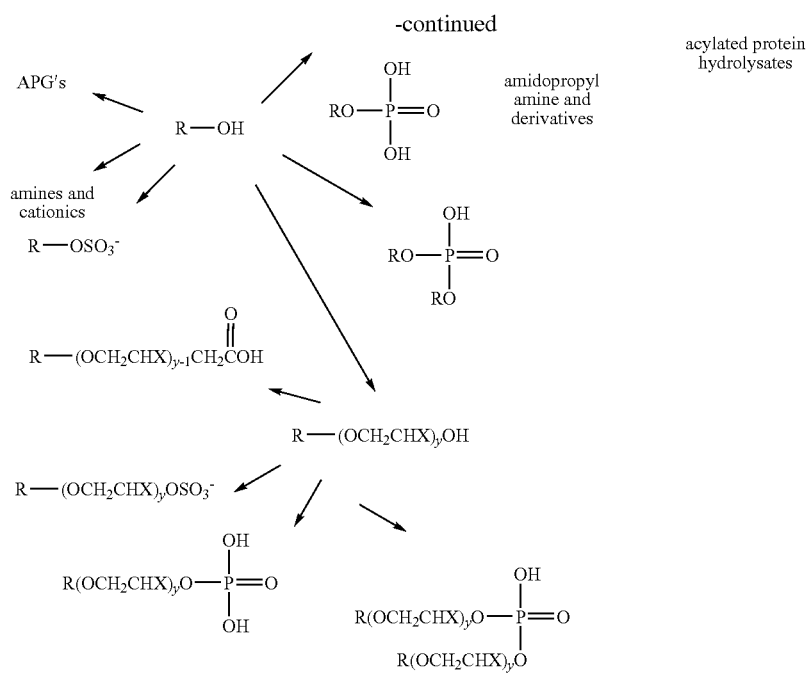

The invention will be illustrated by the following nonlimiting examples.

Ion-Exchange Procedure

Two general procedures for ion-exchange have been employed to prepared metal ion exchanged zeolites: aqueous ion-exchange and solid state ion-exchange.

Aqueous Procedure

To conduct aqueous ion-exchange, a calculated amount of metal salt, for example $Cu(NO_3)_2$ for $Cu^{2+}$ exchange, is dissolved in distilled and deionized water. Then certain amount of $NH_4^+$ form zeolite is added. The weight ratio of the water to the zeolite is about 12. The amount of metal salt added depends on how much $NH_4^+$ cations in the zeolite needs to be exchanged. For example, if 4000 g of zeolite contains 1 mol $NH_4^+$ and an exchange of 20% is desired, then 0.1 mol of $Cu^{2+}$ is needed since 1 mol $Cu^{2+}$ can replace 2 mol of $NH_4^+$. Therefore, 0.1 mol of $Cu(NO_3)_2$ will be added to 48 L water and then 4000 g of the zeolite is added. The pH of the solution is adjusted to 5 with $HNO_3$. With stirring, the whole mixture is heated to 60° C. and maintained for 24 h. The zeolite is separated from the solution by filtration and washed with distilled and deionized water three times, 48 L water each time. The zeolite is filtered, dried at 110° C. overnight and calcined at 550° C. for 6 h in air. An excessive amount of salt can be employed to achieve high degree of exchange.

Solid Procedure

To conduct solid-state ion-exchange, a calculated amount of metal salt, such as $CuCl_2$ for $Cu^{2+}$ exchange, is mixed with dry $H^+$ form zeolite. The mixture is heated in $N_2$ to 550° C. at a rate of 0.5° C./min and maintained at 550° C. for 10 h. The amount of the salt is based on how much $H^+$ needs to be exchanged. After the calcination, the zeolite can be used directly or it can be washed with distilled and deionized water, calcined again at 500° C. for 3 h before use.

Example 1

Alkylation of an Aromatic Compound with Oleic Acid at 250° C. Using $Cu^{2+}$ Exchanged Beta Zeolite 1 g of Cu-Beta and 19.56 g of toluene were loaded into the autoclave reactor. The reactor was purged with $N_2$ three times and charged to 50 psig. With active stirring, the mixture was heated to 250° C. within half an hour and then 10 g of oleic acid was added with a pump in a rate of 5 g/h. The total mole ratio of toluene to oleic acid was about 6. After the addition finished (T=0), the reaction was continued for another 4 h. Reaction results are shown in Table 1. The composition of oleic acid (feed) is also listed in Table 1.

TABLE 1

| Time h | $<=C_{10}$ | $i\text{-}C_{12}^1$ | $C_{12}$ | $i\text{-}C_{14}^1$ | $C_{14}^1$ | $C_{14}$ | $i\text{-}C_{16}^1$ | $C_{16}^1$ | $C_{16}$ | $i\text{-}C_{18}^1$ | $C_{18}^1$ | $C_{18}$ | Lactone | Tolyl-stearic acid |
|---|---|---|---|---|---|---|---|---|---|---|---|---|---|---|
| feed | 0 | 0.2 | 0.1 | 0.6 | 0.5 | 1.9 | 0.7 | 5.0 | 4.1 | 2.0 | 79.6 | 1.9 | 3.5 | 0 |
| 4 | 1.1 | 1.6 | 0.9 | 1.7 | 0.2 | 2.2 | 6.4 | 0.7 | 6.4 | 29.5 | 6.5 | 3.8 | 5.4 | 33.39 |

Example 2

Alkylation of an Aromatic Compound with Oleic Acid at 220° C. Using $Cu^{2+}$ Exchanged Beta Zeolite 1 g of Cu-Beta and 19.56 g of toluene were loaded into the autoclave reactor. The reactor was purged with $N_2$ three times and charged to 50 psig. With active stirring, the mixture was heated to 220° C. within half an hour and then 10 g of oleic acid was added with a pump in a rate of 5 g/h. The total mole ratio of toluene to oleic acid was about 6. After the addition finished (T=0), the reaction was continued for another 7 h with interval sampling for GC analysis.

Reaction results are shown in Table 2.

TABLE 2

| Time H | $\leq C_{10}$ | i-$C_{12}^1$ | $C_{12}$ | i-$C_{14}^1$ | $C_{14}^1$ | $C_{14}$ | i-$C_{16}^1$ | $C_{16}^1$ | $C_{16}$ | i-$C_{18}^1$ | $C_{18}^1$ | $C_{18}$ | Lactone | Tolyl-stearic acid |
|---|---|---|---|---|---|---|---|---|---|---|---|---|---|---|
| 3 | 1.0 | 0.1 | 1.5 | 0.4 | 0 | 2.4 | 1.8 | 0.4 | 5.2 | 26.4 | 12.4 | 3.9 | 10.1 | 32.4 |
| 5 | 0.9 | 0.1 | 1.3 | 0.4 | 0 | 2.2 | 1.1 | 0.2 | 4.6 | 25.6 | 8 | 3.2 | 12.1 | 38.3 |
| 7 | 0.8 | 0 | 1.9 | 0.4 | 0 | 2.9 | 3.5 | 0 | 5.8 | 27.8 | 5.5 | 2.7 | 8.1 | 38.8 |

Example 3

2 g of sulfated zirconia ($SO_4/ZrO_2$, AkzoNobel, 630° C. calcined) and 16.3 g of toluene were loaded into a three-neck glass flask with a magnetic stirrer inside. Nitrogen was introduced into the flask and flew out through a condenser. The reactor was heated over an oil-bath to 150° C. and oleic acid was added in a slow rate. Totally 5 g of oleic acid (Emersol) was added in 2 h. Then the whole mixture was maintained at 150° C. for 48 h under active stirring. After the reactor was cooled to room temperature, the liquid product was separated from the solid catalyst by filtration. The product was analyzed with a GC. Results shown in Table 1. The conversion of $C_{18}^1$ acid was 27.6 wt %, the isomerization selectivity was 24.7 wt % and the alkylation selectivity was 53.6 wt %.

Example 4

1 g of heterophosphotungstic acid catalyst, ($H_{0.5}Cs_{2.5}PW_{12}O_{40}$, 200° C. calcined in $N_2$) and 16.3 g of toluene were loaded into a three-neck glass flask with a magnetic stirrer inside. Nitrogen was introduced into the flask and flew out through a condenser. The reactor was heated over an oil-bath to 150° C. and oleic acid was added in a slow rate. Totally 5 g of oleic acid (Emersol) was added in 5 h and the mole ratio of toluene to oleic acid was about 10. Then the whole mixture was maintained at 150° C. for 48 h under active stirring. After the reactor was cooled to room temperature, the liquid product was separated from the solid catalyst by centrifugal separation. The product was analyzed with a GC. Result is shown in Table 1. The conversion of $C_{18}^1$ acid was 7.2 wt %, the isomerization selectivity was 64.6 wt % and the alkylation selectivity was 6.24 wt %.

Example 5

0.5 g of $La(CF_3SO_3)_3$, a metal triflate, and 18.79 g of xylene were loaded into a three-neck glass flask with a magnetic stirrer inside. Nitrogen was introduced into the flask and flew out through a condenser. The reactor was heated over an oil-bath to 150° C. and oleic acid (Emersol) was added in a slow rate. Totally 5 g of oleic acid was added in half an hour and the mole ratio of xylene to oleic acid was about 10. Then the whole mixture was maintained at 150° C. for 20 h under active stirring. After the reactor was cooled to room temperature, the liquid product was separated from the solid catalyst by filtration. The product was analyzed with a GC. Result is shown in Table 1. The conversion of $C_{18}^1$ acid was 17.1 wt %, the isomerization selectivity was 34.9 wt % and the alkylation selectivity was 2.6 wt %.

Example 6

2 g of HBeta (SAR 50), a 3D large pore acidic zeolite, and 18.79 g of xylene were loaded into a three-neck glass flask with a magnetic stirrer inside. Nitrogen was introduced into the flask and flew out through a condenser. The reactor was heated over an oil-bath to 150° C. and oleic acid (Emersol) was added in a slow rate. Totally 5 g of oleic acid was added in 2 h and then the whole mixture was maintained at 150° C. for 20 h under active stirring. After the reactor was cooled to room temperature, the liquid product was separated from the solid catalyst by filtration. The product was analyzed with a GC. Result is shown in Table 1. The conversion of $C_{18}^1$ acid was 15.9 wt %, the isomerization selectivity was 16.0 wt % and the alkylation selectivity was 25.6 wt %.

TABLE 1

| EX. | <=$C_{10}$ | i-$C_{12}^1$ | $C_{12}$ | i-$C_{14}^1$ | $C_{14}^1$ | $C_{14}$ | i-$C_{16}^1$ | $C_{16}^1$ | $C_{16}$ | i-$C_{18}^1$ | $C_{18}^1$ | $C_{18}$ | Lactone | Tolyl-stearic acid |
|---|---|---|---|---|---|---|---|---|---|---|---|---|---|---|
| Feed | 0.12 | 0.28 | 0.63 | 0.16 | 1.6 | 2.11 | 0.7 | 8.89 | 4.43 | 3.22 | 74.53 | 1.48 | 1.85 | 0 |
| 1 | 0.12 | 0.26 | 1.46 | 0.12 | 1.32 | 2.49 | 0.75 | 7.96 | 4.81 | 3.88 | 68.84 | 0.88 | 3.38 | 3.73 |
| 2 | 0.1 | 0.26 | 2.5 | 0 | 0.18 | 2.32 | 1.23 | 0.29 | 5.38 | 3.92 | 12.87 | 2.61 | 7.34 | 61 |
| 3 | 0.12 | 0.49 | 1.95 | 0.17 | 0.8 | 2.65 | 1.37 | 5.4 | 5.31 | 8.26 | 52.1 | 2.17 | 5.1 | 14.11 |
| 4 | 0.3 | 0 | 1.84 | 0 | 1.17 | 2.46 | 0.83 | 6.74 | 5.23 | 5.03 | 60.83 | 0.83 | 3.96 | 10.78 |
| 5 | 0.18 | 0 | 2.58 | 0 | 1.45 | 2.59 | 1.01 | 7.5 | 5.43 | 6.65 | 63.25 | 5.69 | 2.45 | 1.22 |
| 6 | 0.31 | 0 | 3.14 | 0 | 1.28 | 2.81 | 0.9 | 7.14 | 6.15 | 7.48 | 61.58 | 1.97 | 6.02 | 1.22 |

Example 7

2 g of tungstated zirconia ($WO_3/ZrO_2$, MEL), a metal oxide modified zirconia, and 32.6 g of toluene were loaded into a 135 ml autoclave reactor. The reactor was purged with $N_2$ three times and charged to 50 psig. With active stirring, the mixture was heated to 250° C. within half an hour and then 10 g of oleic acid (Akzo Nobel) was added with a pump in a rate of 5 g/h. After the addition finished (T=0 h), the reaction was maintained for 6 h with interval sampling for GC analysis. Reaction results are shown in Table 2. For the 6 th h sample, the conversion of $C_{18}^1$ acid was 24.3 wt %, the isomerization selectivity was 42.4 wt % and the alkylation selectivity was 14.9 wt %.

TABLE 2

| Time H | <=$C_{10}$ | i-$C_{12}^1$ | $C_{12}$ | i-$C_{14}^1$ | $C_{14}^1$ | $C_{14}$ | i-$C_{16}^1$ | $C_{16}^1$ | $C_{16}$ | i-$C_{18}^1$ | $C_{18}^1$ | $C_{18}$ | Lactone | Tolyl-stearic acid |
|---|---|---|---|---|---|---|---|---|---|---|---|---|---|---|
| Feed | 0 | 0.15 | 0.08 | 0.63 | 0.48 | 1.92 | 0.74 | 4.99 | 4.07 | 1.95 | 79.58 | 1.92 | 3.49 | 0 |
| 1 | 0.1 | 0.14 | 1.44 | 0.13 | 0.43 | 2.29 | 1.06 | 3.89 | 6.56 | 7.17 | 65.8 | 1.06 | 7.15 | 2.78 |
| 2 | 0.03 | 0 | 1.58 | 0 | 0.44 | 2.3 | 1.67 | 3.6 | 6.21 | 7.8 | 64.53 | 1.46 | 7.24 | 3.14 |
| 4 | 0.11 | 0.22 | 1.65 | 0.11 | 0.4 | 2.5 | 1.76 | 3.36 | 6.39 | 9.02 | 61.8 | 2.01 | 7.35 | 3.32 |
| 6 | 0.04 | 0 | 1.62 | 0 | 0.41 | 2.28 | 2.08 | 3.14 | 6.49 | 10.1 | 59.68 | 2.43 | 7.97 | 3.79 |

Example 8

5 g of $WO_3/ZrO_2$ and 32.6 g of toluene were loaded into the autoclave reactor. The reactor was purged with $N_2$ three times and charged to 50 psig. With active stirring, the mixture was heated to 250° C. within half an hour and then 10 g of oleic acid (AkzoNobel) was added with a pump in a rate of 5 g/h. After the addition finished (T=0 h), the reaction was maintained for 8 h with interval sampling for GC analysis. Reaction results are shown in Table 3. For the 8 th h sample, the conversion of $C_{18}^1$ acid was 75.6 wt %, the isomerization selectivity was 45.6 wt % and the alkylation selectivity was 32.5 wt %.

TABLE 3

| Time h | <=$C_{10}$ | i-$C_{12}^1$ | $C_{12}$ | i-$C_{14}^1$ | $C_{14}^1$ | $C_{14}$ | i-$C_{16}^1$ | $C_{16}^1$ | $C_{16}$ | i-$C_{18}^1$ | $C_{18}^1$ | $C_{18}$ | Lactone | Tolyl-stearic acid |
|---|---|---|---|---|---|---|---|---|---|---|---|---|---|---|
| 1 | 0.28 | 0.28 | 1.4 | 0.2 | 0 | 2.67 | 1.79 | 1.94 | 7.04 | 16.9 | 38.8 | 2.79 | 9.33 | 16.61 |
| 2 | 0.19 | 0.11 | 1.73 | 0.45 | 0 | 2.14 | 2.13 | 1.53 | 7.09 | 19.8 | 32.87 | 2.52 | 10.54 | 18.87 |
| 4 | 0.09 | 0 | 1.3 | 0.44 | 0 | 2.2 | 2.36 | 1.14 | 7.19 | 23.5 | 26.1 | 2.06 | 11.26 | 22.38 |
| 6 | 0.11 | 0 | 1.88 | 0.39 | 0 | 2.44 | 2.66 | 0.75 | 7.66 | 26 | 21.2 | 2.02 | 11.16 | 23.74 |
| 8 | 0.14 | 0.07 | 1.87 | 0.56 | 0.16 | 2.32 | 2.96 | 0.71 | 7.85 | 27.73 | 18.28 | 2.04 | 10.93 | 24.38 |

Example 9

2 g of sulfated zirconia, $SO_4/ZrO_2$, and 32.6 g of toluene were loaded into the autoclave reactor. The reactor was purged with $N_2$ three times and charged to 50 psig. With active stirring, the mixture was heated to 250° C. within half an hour and then 10 g of oleic acid (AkzoNobel) was added with a pump in a rate of 5 g/h. After the addition finished (T=0), the reaction was maintained for 8 h with interval sampling for GC analysis. The final product left in the reactor after reaction was distillated to remove toluene and sent for GC-MS and NMR analysis. Reaction results are shown in Table 4. For the 8 th h sample, the conversion of $C_{18}^1$ acid was 81.8 wt %, the isomerization selectivity was 48.6 wt % and the alkylation selectivity was 37.6 wt %.

TABLE 4

| Time h | $<=C_{10}$ | i-$C_{12}^1$ | $C_{12}$ | i-$C_{14}^1$ | $C_{14}^1$ | $C_{14}$ | i-$C_{16}^1$ | $C_{16}^1$ | $C_{16}$ | i-$C_{18}^1$ | $C_{18}^1$ | $C_{18}$ | Lactone | Tolyl-stearic acid |
|---|---|---|---|---|---|---|---|---|---|---|---|---|---|---|
| 1 | 0.42 | 0.25 | 1.21 | 0.63 | 0 | 2.41 | 4.06 | 1.44 | 6.63 | 22.3 | 29.89 | 2.02 | 6.95 | 21.82 |
| 2 | 0.48 | 0 | 1.87 | 0 | 0 | 2.87 | 3.71 | 1 | 7.03 | 24.9 | 25.54 | 1.48 | 5.95 | 25.21 |
| 4 | 0.53 | 0 | 1.83 | 0.43 | 0.21 | 2.23 | 3.97 | 0.67 | 7.19 | 28.3 | 19.82 | 0.96 | 6.15 | 27.7 |
| 6 | 0.55 | 0 | 1.89 | 0.47 | 0.22 | 2.27 | 4.17 | 0.55 | 7.39 | 30.3 | 15.92 | 1.14 | 5.78 | 29.36 |
| 8 | 0.55 | 0.25 | 1.56 | 0 | 0 | 3.01 | 4.42 | 0.54 | 7.43 | 31.3 | 13.44 | 1.12 | 6.37 | 30.05 |

NMR analysis shows that 51 mol % of tolyl group was attached to the long alkyl chain at the para position and 49 mol % was at the ortho position.

Example 10

4 g of sulfated zirconia, $SO_4/ZrO_2$, and 32.6 g of toluene were loaded into the autoclave reactor. The reactor was purged with $N_2$ three times and charged to 50 psig. With active stirring, the mixture was heated to 250° C. within half an hour and then 10 g of oleic acid (Akzo Nobel) was added with a pump in a rate of 5 g/h. After the addition finished (T=0), the reaction was maintained for 4 h with interval sampling for GC analysis. Reaction results are shown in Table 5. For the 4 th h sample, the conversion of $C_{18}^1$ acid was 92.2 wt %, the isomerization selectivity was 32.1 wt % and the alkylation selectivity was 54.1 wt %.

TABLE 5

| Time h | $<=C_{10}$ | i-$C_{12}^1$ | $C_{12}$ | i-$C_{14}^1$ | $C_{14}^1$ | $C_{14}$ | i-$C_{16}^1$ | $C_{16}^1$ | $C_{16}$ | i-$C_{18}^1$ | $C_{18}^1$ | $C_{18}$ | Lactone | Tolyl-stearic acid |
|---|---|---|---|---|---|---|---|---|---|---|---|---|---|---|
| 1 | 0.74 | 0 | 1.79 | 1.4 | 0.25 | 2.32 | 3.79 | 1.49 | 7.14 | 24.9 | 14.2 | — | 4.28 | 37.74 |
| 2 | 1.13 | 0.94 | 2.3 | 1.64 | 0.21 | 2.46 | 4.28 | 0 | 8.53 | 24.6 | 6.75 | — | 3.62 | 43.53 |
| 3 | 0.88 | 0.96 | 2.37 | 1.7 | 0 | 0.2 | 5 | 0 | 7.55 | 23.3 | 5.69 | — | 5.83 | 46.49 |
| 4 | 0.88 | 1 | 2.74 | 1.62 | 0.22 | 2.47 | 5.33 | 0 | 7.59 | 22.8 | 5.5 | — | 3.26 | 46.59 |

The peak of stearic acid was not well resolved from those of oleic acid isomers.

The product left in the reactor after reaction was separated from solid catalyst by filtration, distillated to remove toluene.

Example 11

2 g of used catalyst from Example 8 and 32.6 g of toluene were loaded into the autoclave reactor. The reactor was purged with $N_2$ three times and charged to 50 psig. With active stirring, the mixture was heated to 250° C. within half an hour and then 10 g of oleic acid (Akzo Nobel) was added with a pump in a rate of 5 g/h. After the addition finished (T=0), the reaction was maintained for 8 h with interval sampling for GC analysis. Results are shown in Table 6. For the 8 th h sample, the conversion of $C_{18}^1$ acid was 45 wt %, the isomerization selectivity was 64.4 wt % and the alkylation selectivity was 14 wt %.

TABLE 6

| Time h | <=$C_{10}$ | i-$C_{12}^1$ | $C_{12}$ | i-$C_{14}^1$ | $C_{14}^1$ | $C_{14}$ | i-$C_{16}^1$ | $C_{16}^1$ | $C_{16}$ | i-$C_{18}^1$ | $C_{18}^1$ | $C_{18}$ | Lactone | Tolyl-stearic acid |
|---|---|---|---|---|---|---|---|---|---|---|---|---|---|---|
| 1 | 0.16 | 0.25 | 1.48 | 0 | 0 | 2.41 | 1.52 | 3.63 | 6.25 | 13.1 | 57.5 | 2.15 | 7.67 | 3.86 |
| 4 | 0.11 | 0 | 2.08 | 0 | 0 | 2.43 | 2.02 | 2.5 | 6.87 | 19.6 | 49.28 | 2.95 | 7.17 | 4.95 |
| 8 | 0.15 | 0 | 1.83 | 0 | 0 | 2.4 | 2.32 | 2.15 | 6.9 | 24.6 | 43.09 | 2.3 | 7.7 | 6.53 |

The used catalyst had a much lower activity for the addition reaction than the fresh one, but its isomerization activity was barely affected. This could be due to the coke formed or the moisture absorbed during the second loading, which mainly deactivated the strong acid site for the addition reaction.

Example 12

4 g of sulfated zirconia, $SO_4/ZrO_2$, and 32.6 g of toluene were loaded into the autoclave reactor. The reactor was purged with $N_2$ three times and charged to 50 psig. With active stirring, the mixture was heated to 180° C. within half an hour and then 10 g of oleic acid (Akzo Nobel) was added with a pump in a rate of 5 g/h. After the addition finished (T=0), the reaction was maintained for 8 h with interval sampling for GC analysis. Reaction results are shown in Table 7. For the 8 th h sample, the conversion of $C_{18}^1$ acid was 60.9 wt %, the isomerization selectivity was 28.3 wt % and the alkylation selectivity was 56.7 wt %.

TABLE 7

| Time h | <=$C_{10}$ | i-$C_{12}^1$ | $C_{12}$ | i-$C_{14}^1$ | $C_{14}^1$ | $C_{14}$ | i-$C_{16}^1$ | $C_{16}^1$ | $C_{16}$ | i-$C_{18}^1$ | $C_{18}^1$ | $C_{18}$ | Lactone | Tolyl-stearic acid |
|---|---|---|---|---|---|---|---|---|---|---|---|---|---|---|
| 1 | 0.27 | 0 | 1.88 | 0 | 0 | 2.38 | 1.22 | 2.64 | 6.36 | 10.1 | 46.38 | 1.85 | 5.84 | 21.1 |
| 2 | 0.28 | 0 | 2.29 | 0 | 0 | 2.33 | 1.28 | 2.13 | 6.44 | 10.1 | 40.86 | 2.44 | 6.14 | 25.68 |
| 4 | 0.34 | 0.15 | 2.11 | 0 | 0 | 2.33 | 1.45 | 1.79 | 6.44 | 12 | 35.99 | 2.4 | 6.38 | 28.67 |
| 6 | 0.35 | 0 | 2.45 | 0.15 | 0 | 2.33 | 1.52 | 1.49 | 6.48 | 13.5 | 32 | 2.13 | 6.46 | 31.16 |
| 8 | 0.25 | 0.25 | 2.26 | 0.13 | 0.24 | 2.07 | 1.62 | 1.26 | 6.41 | 14.6 | 28.54 | 2.02 | 6.95 | 33.44 |

Example 13

The catalyst from Example 10 was separated by filtration and dried at 100° C. for 4 h. Then it was calcined in air at 450° C. for 5 h. Two grams of this calcined catalyst and 32.6 g of toluene were loaded into the autoclave reactor. The reactor was purged with $N_2$ three times and charged to 50 psig. With active stirring, the mixture was heated to 250° C. within half an hour and then 10 g of oleic acid (Akzo Nobel) was added with a pump in a rate of 5 g/h. After the addition finished (T=0), the reaction was maintained for 8 h with interval sampling for GC analysis. For the 8 th h sample, the conversion of $C_{18}^1$ acid was 82.7 wt %, the isomerization selectivity was 51.1 wt % and the alkylation selectivity was 37.1 wt %. Compared with Example 7, results shown in Table 8 indicate that the activity can be completely recovered by calcination in air.

TABLE 8

| Time h | <=$C_{10}$ | i-$C_{12}^1$ | $C_{12}$ | i-$C_{14}^1$ | $C_{14}^1$ | $C_{14}$ | i-$C_{16}^1$ | $C_{16}^1$ | $C_{16}$ | i-$C_{18}^1$ | $C_{18}^1$ | $C_{18}$ | Lactone | Tolyl-stearic acid |
|---|---|---|---|---|---|---|---|---|---|---|---|---|---|---|
| 1 | 0.18 | 0 | 1.15 | 0.28 | 0 | 2.61 | 2.69 | 1.71 | 6.82 | 23.17 | 29.44 | 1.93 | 5.76 | 24.26 |
| 2 | 0.11 | 0 | 1.52 | 0.28 | 0 | 2.66 | 3.12 | 1.32 | 7.04 | 26.05 | 25.13 | 1.62 | 6 | 25.15 |
| 4 | 0.2 | 0 | 1.4 | 0.34 | 0 | 2.66 | 3.24 | 1.16 | 7.14 | 29.06 | 19.87 | 0.92 | 6.74 | 27.27 |
| 6 | 0.23 | 0 | 1.33 | 0.81 | 0 | 2.22 | 3.51 | 0.99 | 7.32 | 31.4 | 15.37 | 0.71 | 6.72 | 29.39 |
| 8 | 0.26 | 0 | 1.6 | 0.72 | 0 | 2.45 | 3.67 | 0 | 8.06 | 33.1 | 12.78 | 0.93 | 6.45 | 29.98 |

Example 14

2 g of sulfated zirconia, $SO_4/ZrO_2$, and 19.56 g of toluene were loaded into the autoclave reactor. The reactor was purged with $N_2$ three times and charged to 50 psig. With active stirring, the mixture was heated to 250° C. within half an hour and then 10 g of oleic acid (Akzo Nobel) was added with a pump in a rate of 5 g/h. The total mole ratio of toluene to oleic acid was about 6. After the addition finished (T=0), the reaction was maintained for 8 h with interval sampling for GC analysis. Reaction results are shown in Table 9. For the 8 th h sample, the conversion of $C_{18}^1$ acid was 89.5 wt %, the isomerization selectivity was 42.8 wt % and the alkylation selectivity was 44.6 wt %.

TABLE 9

| Time h | $<=C_{10}$ | $i\text{-}C_{12}^1$ | $C_{12}$ | $i\text{-}C_{14}^1$ | $C_{14}^1$ | $C_{14}$ | $i\text{-}C_{16}^1$ | $C_{16}^1$ | $C_{16}$ | $i\text{-}C_{18}^1$ | $C_{18}^1$ | $C_{18}$ | Lactone | Tolyl-stearic acid |
|---|---|---|---|---|---|---|---|---|---|---|---|---|---|---|
| 1 | 0.22 | 0 | 1.47 | 0.41 | 0 | 2.76 | 3.3 | 1.57 | 7.08 | 25.46 | 25.61 | 1.34 | 5.67 | 25.11 |
| 4 | 0.43 | 0 | 1.72 | 0.49 | 0 | 2.99 | 4.15 | 0 | 8.5 | 30.46 | 12.24 | 0.98 | 5.74 | 32.3 |
| 8 | 0.25 | 0.6 | 1.44 | 0.98 | 0.19 | 2.37 | 4.82 | 0 | 7.92 | 29.58 | 7.6 | 0.82 | 5.29 | 38.14 |

Example 15

2 g of sulfated zirconia, $SO_4/ZrO_2$, and 9.78 g of toluene were loaded into the autoclave reactor. The reactor was purged with $N_2$ three times and charged to 50 psig. With active stirring, the mixture was heated to 250° C. within half an hour and then 10 g of oleic acid (AkzoNobel) was added with a pump in a rate of 5 g/h. The total mole ratio of toluene to oleic acid was about 3. After the addition finished (T=0), the reaction was maintained for 8 h with interval sampling for GC analysis. Reaction results are shown in Table 10. For the 8 th h sample, the conversion of $C_{18}^1$ acid was 65.8 wt %, the isomerization selectivity was 61.6 wt % and the alkylation selectivity was 19.5 wt %.

TABLE 10

| Time h | $<=C_{10}$ | $i\text{-}C_{12}^1$ | $C_{12}$ | $i\text{-}C_{14}^1$ | $C_{14}^1$ | $C_{14}$ | $i\text{-}C_{16}^1$ | $C_{16}^1$ | $C_{16}$ | $i\text{-}C_{18}^1$ | $C_{18}^1$ | $C_{18}$ | Lactone | Tolyl-stearic acid |
|---|---|---|---|---|---|---|---|---|---|---|---|---|---|---|
| 1 | 0.05 | 0.18 | 1.09 | 0 | 0.45 | 2.12 | 2.07 | 3.04 | 6.79 | 16.4 | 48.39 | 2.85 | 8.22 | 8.35 |
| 4 | 0.05 | 0.16 | 1.14 | 0.09 | 0 | 2.67 | 3.15 | 1.76 | 7.37 | 27.46 | 33.92 | 1.95 | 7.97 | 12.31 |
| 8 | 0.06 | 0.22 | 1.6 | 0 | 0 | 2.76 | 3.56 | 1.37 | 7.89 | 33.16 | 26.33 | 2.1 | 7.86 | 13.09 |

Example 16

1 g of $Cu^{2+}$ exchanged Beta and 19.56 g of toluene were loaded into the autoclave reactor. The reactor was purged with $N_2$ three times and charged to 50 psig. With active stirring, the mixture was heated to 250° C. within half an hour and then 10 g of oleic acid was added with a pump in a rate of 5 g/h. The total mole ratio of toluene to oleic acid was about 6. After the addition finished (T=0), the reaction was continued for another 4 h. Reaction results are shown in Table 1. The composition of oleic acid (feed) is also listed in Table 11.

TABLE 11

| Time h | $<=C_{10}$ | $i\text{-}C_{12}^1$ | $C_{12}$ | $i\text{-}C_{14}^1$ | $C_{14}^1$ | $C_{14}$ | $i\text{-}C_{16}^1$ | $C_{16}^1$ | $C_{16}$ | $i\text{-}C_{18}^1$ | $C_{18}^1$ | $C_{18}$ | lactone | Tolyl stearic acid |
|---|---|---|---|---|---|---|---|---|---|---|---|---|---|---|
| 4 | 1.1 | 1.6 | 0.9 | 1.7 | 0.2 | 2.2 | 6.4 | 0.7 | 6.4 | 29.5 | 6.5 | 3.8 | 5.4 | 33.39 |

Example 17

1 g of $Cu^{2+}$ exchanged Beta and 19.56 g of toluene were loaded into the autoclave reactor. The reactor was purged with $N_2$ three times and charged to 50 psig. With active stirring, the mixture was heated to 220° C. within half an hour and then 10 g of oleic acid was added with a pump in a rate of 5 g/h. The total mole ratio of toluene to oleic acid was about 6. After the addition finished (T=0), the reaction was continued for another 7 h with interval sampling for GC analysis. Reaction results are shown in Table 12.

TABLE 12

| Time h | <=$C_{10}$ | i-$C_{12}^1$ | $C_{12}$ | i-$C_{14}^1$ | $C_{14}^1$ | $C_{14}$ | i-$C_{16}^1$ | $C_{16}^1$ | $C_{16}$ | i-$C_{18}^1$ | $C_{18}^1$ | $C_{18}$ | lactone | Tolyl stearic acid |
|---|---|---|---|---|---|---|---|---|---|---|---|---|---|---|
| 3 | 1.0 | 0.1 | 1.5 | 0.4 | 0 | 2.4 | 1.8 | 0.4 | 5.2 | 26.4 | 12.4 | 3.9 | 10.1 | 32.4 |
| 5 | 0.9 | 0.1 | 1.3 | 0.4 | 0 | 2.2 | 1.1 | 0.2 | 4.6 | 25.6 | 8 | 3.2 | 12.1 | 38.3 |
| 7 | 0.8 | 0 | 1.9 | 0.4 | 0 | 2.9 | 3.5 | 0 | 5.8 | 27.8 | 5.5 | 2.7 | 8.1 | 38.8 |

Comparative Example 1

2 g of $SO_4/ZrO_2$ and 10 g of oleic acid (Akzo Nobel) were loaded into the autoclave reactor. The reactor was purged with $N_2$ three times and charged to 50 psig. With active stirring, the mixture was heated to 250° C. within half an hour. Then the reaction was maintained for 4 h. After being separated from the solid catalyst by filtration with heat, the liquid product solidified at room temperature. It may contain high molecular weight components, which cannot be identified by the used GC method. GC analysis result is shown in Table 13. The conversion of $C_{18}^1$ acid was 27.6 wt %, the isomerization selectivity was 79.4 wt %.

TABLE 13

| <=$C_{10}$ | i-$C_{12}^1$ | $C_{12}$ | i-$C_{14}^1$ | $C_{14}^1$ | $C_{14}$ | i-$C_{16}^1$ | $C_{16}^1$ | $C_{16}$ | i-$C_{18}^1$ | $C_{18}^1$ | $C_{18}$ | lactone |
|---|---|---|---|---|---|---|---|---|---|---|---|---|
| 0.28 | 0.14 | 1.06 | 0.23 | 0 | 2.15 | 1.82 | 2.67 | 7.14 | 18.41 | 53.98 | 3.5 | 8.62 |

This example demonstrates the isomerization activity of the sulfated zirconia catalyst itself in the absence of aromatic compound. Comparing with examples given above, it is evident that addition of aromatic compound promotes isomerization at the same time of alkylation.

Comparative Example 2

2 g of $SO_4/ZrO_2$, 32.6 g of toluene and 10 g of oleic acid (Akzo Nobel) were loaded into the autoclave reactor. The reactor was purged with $N_2$ three times and charged to 50 psig. With active stirring, the mixture was heated to 250° C. within half an hour. This time was considered as T=0. Then the reaction was maintained for 8 h with interval sampling for GC analysis. Result is shown in Table 14. For the 8 th h sample, the conversion of $C_{18}^1$ acid was 59.2 wt %, the isomerization selectivity was 63.3 wt % and the alkylation selectivity was 17.3 wt %.

TABLE 14

| Time h | <=$C_{10}$ | i-$C_{12}^1$ | $C_{12}$ | i-$C_{14}^1$ | $C_{14}^1$ | $C_{14}$ | i-$C_{16}^1$ | $C_{16}^1$ | $C_{16}$ | i-$C_{18}^1$ | $C_{18}^1$ | $C_{18}$ | Lactone | Tolyl-stearic acid |
|---|---|---|---|---|---|---|---|---|---|---|---|---|---|---|
| 1 | 0.24 | 0.07 | 1.03 | 0 | 0.3 | 2.09 | 2.16 | 2.43 | 6.72 | 15.48 | 53.93 | 2.87 | 7.8 | 4.88 |
| 2 | 0.25 | 0 | 1.19 | 0 | 0.23 | 2.2 | 1.94 | 2.57 | 6.74 | 19.38 | 48.17 | 2.94 | 8.3 | 6.09 |
| 4 | 0 | 0 | 1.19 | 0 | 0 | 2.38 | 2.41 | 2.03 | 6.84 | 24.93 | 40.95 | 2.39 | 8.95 | 7.93 |
| 6 | 0.14 | 0.12 | 1.37 | 0 | 0.31 | 2.09 | 2.69 | 1.97 | 6.55 | 27.87 | 36.07 | 2.02 | 9.35 | 9.45 |
| 8 | 0.16 | 0 | 1.46 | 0 | 0 | 2.43 | 2.91 | 1.08 | 7.34 | 31.01 | 31.6 | 1.64 | 9.84 | 10.53 |

In this example, instead of being mixed with the catalyst and toluene before the reaction, the oleic acid was added gradually into the reactor. Gradually addition of oleic acid resulted in higher oleic acid conversion and higher yield of the alkylated product.

The invention claimed is:

1. A process for the arylation and isomerization of unsaturated linear fatty acids and/or alkyl esters to their aryl branched counterparts which comprises arylating and isomerizing a feedstock in the presence of at least one acidic zeolite catalyst, wherein said acidic catalyst comprises at least one metal ion exchanged acidic catalyst, wherein said catalyst comprises at least one non-zero valent metal ion, wherein said feedstock comprises unsaturated linear fatty acids, alkyl esters of unsaturated fatty acids or mixtures thereof and at least one aromatic compound.

2. The process according to claim 1 wherein the feedstock comprises of at least 50% by weight of unsaturated fatty acids, alkyl esters of unsaturated fatty acids or mixtures thereof.

3. The process of claim 2 wherein the feedstock comprises of at least 70% by weight oleic acid.

4. The process of claim 1 wherein the feedstock further comprises at least one aryl compound.

5. The process of claim 4 wherein said aryl compound is optionally substituted with at least one heteroatom.

6. The process of claim 4 wherein said aryl compound optionally contains at least one heteroatom in its cyclic ring structure.

7. The process of claim 4 wherein said aryl compound is selected from the group consisting essentially of benzene, toluene, xylene, cumene, aniline, phenol, cymene, styrene, mesitylene, mixtures thereof and the like.

8. The process of claim 1 wherein said non-zero valent metal ion is selected from the group consisting essentially of monovalent metal, divalent metal, trivalent metal, tetravalent metal, pentavalent metal, hexavalent metal and mixtures thereof.

9. The process of claim 8 wherein said higher valent metal is selected from the group consisting Lie, $Cu^+$, $Rh^+$, $Ir^+$, $Mg^{2+}$, $Ca^{2+}$, $Mn^{2+}$, $Fe^{2+}$, $Co^{2+}$, $Ni^{2+}$, $Cu^{2+}$, $Zn^{2+}$, $Sr^{2+}$, $Mo^{2+}$, $Pd^{2+}$, $Sn^{2+}$, $Pt^{2+}$, $Sc^{3+}$, $Cr^{3+}$, $Fe^{3+}$, $Co^{3+}$, $Ga^{3+}$, $Y^{3+}$, $Nb^{3+}$, $Ru^{3+}$, $Rh^{3+}$, $Ir^{3+}$, $Bi^{3+}$, $Ti^{4+}$, $Mn^{4+}$, $Zr^{4+}$, $Mo^{4+}$, $Sn^{4+}$, $V^{5+}$, $Nb^{5+}$, $Mo^{6+}$, mixtures thereof and the like.

10. The process of claim 1 wherein the metal ion concentration is at least 0.001% of the exchange capacity of the catalyst support.

11. The process of claim 10 wherein the metal ion concentration is at least 0.5% of the exchange capacity.

12. The process of claim 10 wherein the metal ion concentration is in the range of 0.001 to above 200% exchange level.

* * * * *

UNITED STATES PATENT AND TRADEMARK OFFICE
CERTIFICATE OF CORRECTION

PATENT NO.      : 7,619,103 B2                           Page 1 of 1
APPLICATION NO. : 10/565549
DATED           : November 17, 2009
INVENTOR(S)     : Zhang et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 427 days.

Signed and Sealed this

Twenty-sixth Day of October, 2010

David J. Kappos
*Director of the United States Patent and Trademark Office*